(12) United States Patent
Sachdeva et al.

(10) Patent No.: US 8,846,616 B1
(45) Date of Patent: Sep. 30, 2014

(54) ALPHA-MELANOCYTE STIMULATING HORMONE AS TOPICAL ANTI-INFLAMMATORY AGENT FOR THE TREATMENT OF ALLERGIC CONTACT DERMATITIS AND ECZEMA

(75) Inventors: Mandip Singh Sachdeva, Tallahassee, FL (US); Cheryl Armstrong, Little Rock, AK (US); John Ansel, Little Rock, AR (US); Melissa A. Brown, legal representative, Little Rock, AR (US)

(73) Assignees: Florida Agricultural and Mechanical University, Tallahassee, FL (US); The Board of Trustees at the University of Arkansas, Little Rock, AR (US)

( * ) Notice: Subject to any disclaimer, the term of this patent is extended or adjusted under 35 U.S.C. 154(b) by 638 days.

(21) Appl. No.: 12/942,369

(22) Filed: Nov. 9, 2010
(Under 37 CFR 1.47)

Related U.S. Application Data (60) Provisional application No. 61/280,820, filed on Nov. 9, 2009.

(51) Int. Cl.
*A61K 38/34* (2006.01)
*A61K 47/10* (2006.01)
*A61K 47/22* (2006.01)

(52) U.S. Cl.
USPC .......... 514/10.7; 514/423; 514/723; 514/947; 514/18.7; 424/78.05

(58) Field of Classification Search
None
See application file for complete search history.

(56) References Cited

U.S. PATENT DOCUMENTS

| 4,874,744 | A | * | 10/1989 | Nordlund et al. | ............ 514/10.7 |
| 2005/0025723 | A1 | * | 2/2005 | Lipton | ............................ 424/59 |
| 2006/0122282 | A1 | * | 6/2006 | Leonard | ........................ 514/690 |
| 2009/0005667 | A1 | * | 1/2009 | Cui et al. | ...................... 600/395 |

FOREIGN PATENT DOCUMENTS

IN        200400681 I3  *  9/2006

OTHER PUBLICATIONS

Guo et al. Protein tolerance to random amino acid change. Proc Natl Acad Sci U S A. Jun. 22, 2004;101(25):9205-10. Epub Jun. 14, 2004.*
Hiltz et al. Anti-inflammatory activity of alpha-MSH(11-13) analogs: influences of alteration in stereochemistry. Peptides. Jul.-Aug. 1991;12(4):767-71.*
Health and Nutrition Product Guide, "Pharmasolve® Drug Solubilizer". PharmaGuide (International Specialty Products, a division of Ashland Inc.): p. 9. 2008.*
Escobar-Chávez et al. In vivo skin permeation of sodium naproxen formulated in pluronic F-127 gels: effect of Azone and Transcutol. Drug Dev Ind Pharm. May 2005;31(4-5):447-54.*
Karande et al. Insights into synergistic interactions in binary mixtures of chemical permeation enhancers for transdermal drug delivery. J Control Release. Sep. 28, 2006;115(1):85-93. Epub Jul. 6, 2006.*
Brzoska T., Luger T.A., Maaser C, Abels C., Bohm M. Alpha-melanocyte-stimulating hormone and related tripeptides: biochemistry, anti-inflammatory and protective effects in vitro and in vivo, and future perspectives for the treatment of immune-mediated inflammatory diseases. Endocr Rev 2008:29:581-602.
Bohm M. Luger T.A., Tobin D.J. Garcia-Borron J.C. Melanocortin receptor ligands: new horizons for skin biology and clinical dermatology. J. Invest Dermatol 2006: 126: 1966-1975.
Bhardwaj R.S., Schwarz A., Becher E., et al. Pro-opiomelanocortin-derived peptides induce IL-10 production in human monocytes. J. Immunol 1996: 156: 2517-2521.
Luger T.A., Scholzen T.E., Brzoska T., Bohm M. New insights into the functions of alpha-MSH and related peptides in the immune system. Ann N.Y. Acad. Sci. 2003: 994: 133-140.
Luger T.A., Scholzen T., Grabbe S. The role of alpha-melanocyte-stimulating hormone in cutaneous biology. J. Investig Dermatol Symp. Proc. 1997: 2: 87-93.
Berger T. G., Duvic M., Van Voorhees A. S., VanBeek M.J., Frieden I.J. The use of topical calcineurin inhibitors in dermatology: safety concerns. Report of the American Academy of Dermatology Association Task Force. J Am Acad Dermatol 2006: 54: 818-823.
Shaw D. W., Eichenfield L.F., Shainhouse T., Maibach H.I. Allergic contact dermatitis from tacrolimus. J Am Acad Dermatol 2004: 50: 962-965.
Luger T.A., Brzoska T. alpha-MSH related peptides: a new class of anti-inflammatory and immunomodulating drugs. Ann Rheum Dis 2007: 66 Suppl 3: iii52-55.
Bohm et al., 2004, Proc. Nat'l Acad: Sci., 279: 6954-6966.
Prabhu N. V., Perkyns J.S., Pettitt B.M. Modeling of alpha-MSH conformations with implicit solvent. J Pept Res 1999: 54: 394-407.
Schacke H., Docke W.D., Asadullah K. Mechanisms involved in the side effects of glucocorticoids. Pharmacol Ther 2002: 96: 23-43.
Sawyer, 1980. Proc. Nat'l Acad. Sci 77: 5754-5758.

* cited by examiner

*Primary Examiner* — David Romeo
(74) *Attorney, Agent, or Firm* — Hugh McTavish (57) ABSTRACT

A method is presented for treating an inflammatory skin disorder in a human comprising: topically applying to the skin a composition comprising alpha-melanocyte stimulating hormone (αMSH) or an αMSH analog in an amount effective to reduce skin inflammation in the human.

12 Claims, 4 Drawing Sheets

SEQUENCE LISTING

```
<160> NUMBER OF SEQ ID NOS: 1

<210> SEQ ID NO 1
<211> LENGTH: 13
<212> TYPE: PRT
<213> ORGANISM: Homo sapiens

<400> SEQUENCE: 1

Ser Tyr Ser Met Glu His Phe Arg Trp Gly Lys Pro Val
1               5                   10
```

ALPHA-MELANOCYTE STIMULATING HORMONE AS TOPICAL ANTI-INFLAMMATORY AGENT FOR THE TREATMENT OF ALLERGIC CONTACT DERMATITIS AND ECZEMA

This application claims priority under 35 U.S.C. §119(e) from U.S. provisional patent application 61/280,820, filed Nov. 9, 2009.

GOVERNMENT SUPPORT

This invention was made with government support under grant S11 AR47455 awarded by the United States National Institutes of Health. The government has certain rights in the invention.

BACKGROUND

The neuropeptide α-melanocyte stimulating hormone (α-MSH) is an endogenous peptide hormone which has been found to exert anti-inflammatory responses in many organ systems, including the skin. α-MSH is generated from proteolytic cleavage of the precursor hormone proopiomelanocortin (POMC), which is also the precursor for the peptide hormones adrenocorticotrophin (ACTH), β-MSH, and γ-MSH (1). These peptide hormones, called melanocortins, were originally described for their pigment-inducing capabilities, but have since been implicated in many other protective processes. POMC and its derivatives are primarily products of the pituitary gland and hypothalamus but have also been shown to be produced locally in the skin (2, 3). α-MSH is endogenous to humans and primarily binds to the melanocortin receptor MC-1R, which is expressed in endothelial cells, fibroblasts, keratinocytes, and melanocytes in the skin (4) as well as in other cells such as monocytes, lymphocytes, and neutrophils (1). MC-4R, which is reportedly expressed in dermal papilla cells, and MC-5R, which has been found to be expressed in sebocytes and skin mast cells, also bind α-MSH (5). It is thought that α-MSH exerts its anti-inflammatory actions primarily by binding to MC-Rs but also through additional effector pathways such as antagonism to IL-1β(1). α-MSH has been shown to exhibit an array of immunosuppressive activities in vitro (6,10).

Despite decades of research, few agents have been successfully developed for eczematous inflammatory disorders. Topical corticosteroids have been extensively developed and utilized clinically to treat a wide range of inflammatory skin disorders for several decades but have many potential side effects that are exacerbated with continual use (11). Recently, calcineurin inhibitors such as tacrolimus and pimecrolimus have been clinically available to use as alternative nonsteroidal topical treatment agents; however, these compounds also have potential harmful side effects, and the FDA has issued a black box warning based on evidence that they are potentially carcinogenic (12-14).

New treatments for eczematous inflammatory disorders and other inflammatory skin disorders are needed as alternatives to corticosteroids, tacrolimus, and pimecrolimus, each of which have problematic side effects.

SUMMARY

The invention provides a pharmaceutical formulation for topical administration comprising α-MSH or analogues of α-MSH to treat inflammatory skin disorders, particularly eczematous inflammatory disorders and allergic contact dermatitis.

The formulations were surprisingly effective in reducing inflammation in a mouse model of allergic contact dermatitis. They were substantially more effective than tacrolimus ointment (PROTOPIC), and nearly as effective as the corticosteroid betamethasone.

It was also surprisingly found that absorption of α-MSH into the skin was much better in a formulation with TRANSCUTOL and 1-methyl-pyrrolidone (NMP) than in formulations lacking these ingredients.

One embodiment of the invention provides a method of treating an inflammatory skin disorder in a human comprising: topically applying to the skin a composition comprising alpha-melanocyte stimulating hormone (αMSH) or an αMSH analogue in an amount effective to reduce skin inflammation in the human.

Another embodiment provides a topical pharmaceutical composition comprising alpha-melanocyte stimulating hormone (αMSH) or an αMSH analogue in an amount effective to reduce skin inflammation in the human.

BRIEF DESCRIPTION OF THE DRAWINGS

FIG. 1. In vivo determination of a topical formulation of full-length α-MSH with efficacy in the treatment of established ACD. The efficacy of various α-MSH formulations is determined by the decrease in thickness from 100% as well as the difference from the effect of the corresponding matched vehicle. The data represent the difference in thickness (%) between the hapten-challenged ear (treated) and the unchallenged ear (dosed with matched vehicles only) of the same mouse 24 hours following the first treatment, and each bar represents the average response of 5 mice within a treatment group. 100% indicates ear swelling immediately before the first treatment (normalized), and 0% indicates the average thickness of the unchallenged ears within each group. Treatment with dexamethasone (white bars) is the positive control within each experimental group. All values are expressed as mean±relative error based on SD.

FIG. 3. A topical formulation of full-length α-MSH was as effective in the treatment of ACD as currently available topical agents The data represent percent change in ear swelling over time according to the following topical treatments: the α-MSH formulation (-▲-), formulation-matched vehicles without α-MSH (-■-), dexamethasone in a matched formulation (--•--), Betamethasone ointment (--○--), Protopic® ointment (-Δ-), and a no treatment group (-□-). Ears were measured 24, 28, 72, and 96 hours after challenge with DNFB and treated 24, 30, 48, 54, 72, and 78 hours after challenge. The data represent the difference in thickness (%) between the hapten-challenged ear (treated ACD) and the unchallenged ear (normal), and each value represents 5 mice in a representative experiment. 100% indicates the total swelling 24 hours following challenge with DNFB, and 0% indicates the average thickness of the normal ears within each treatment group. All values are expressed as mean±SEM.

µm) were stained with hematoxylin and eosin and visualized with a 20× dry objective. Tissue samples in the left column are from normal ears not challenged with DNFB. Tissue samples in the right column are from ears challenged with DNFB to induce ACD and then treated 24, 30, 48, 54, 72, and 78 hours after challenge. Betamethasone ointment served as the positive control. No treatment and treatment with formulation-matched vehicles served as negative controls. Measurements of thickness were made at 5 equidistant points on each of the H&E sections. All values are expressed as mean±SD of the five data points on the same ear. All differences were statistically significant as determined by ANOVA for pair-wise comparison (P<0.05).

DETAILED DESCRIPTION

One embodiment of the invention provides a method of treating an inflammatory skin disorder in a human comprising: topically applying to the skin a composition comprising alpha-melanocyte stimulating hormone (αMSH) or an αMSH analogue in an amount effective to reduce skin inflammation in the human.

Another embodiment provides a topical pharmaceutical, composition comprising alpha-melanocyte stimulating hormone (αMSH) or an αMSH analogue in an amount effective to reduce skin inflammation in the human.

In specific embodiments, the inflammatory skin disorder is allergic contact dermatitis.

In specific embodiments, the inflammatory skin disorder is eczema or an eczematous inflammatory disorder. The term "eczematous inflammatory disorder" as used herein includes atopic dermatitis, allergic contact dermatitis, irritant dermatitis, sunburn, and nummular dermatitis.

In specific embodiments, the inflammatory skin disorder is an established inflammatory skin disorder. By this it is meant that the inflammatory skin disorder is established before treatment begins. That is, the active agent is not used prophylactically before the dermatitis exists.

Wild-type alpha-melanocyte stimulating hormone has the structure Ac-Ser-Tyr-Ser-Met-Glu-His-Phe-Arg-Trp-Gly-Lys-Pro-Val (Ac-SEQ ID NO:1).

Thus, the term "αMSH" as used herein refers to SEQ ID NO:1, optionally N-acetylated and optionally C-amidated.

Analogues of αMSH include the C-terminal tripeptide of αMSH - KPV --- and its variants dKPV, KPdV, KdPV, and dKPdV. Other analogues are KPT and KdPT, where the terminal valine is replaced with the more hydrophilic threonine. In all these peptides, a (d), e.g., in KdPT, refers to a D-streoisomer. So, for instance, KdPT refers to L-Lys-D-Pro-L-Thr. In each of these, the N terminal residue may optionally be N-acetylated, and the C-terminal residue may optionally be C-amidated.

Another analogue is [Nle4,d-Phe7]αMSH, where Met4 is replaced by norleucine, and Phe7 is the D stereoisomer instead of the natural stereoisomer.

Thus, one group of analogues of αMSH are KPV, KPT, and [Nle4,d-Phe7]αMSH, and variants of those where one or more of the amino acids of those three peptides is replaced with the corresponding D-amino acid. It also includes the corresponding reverse D sequence of KPV, KPT, and αMSH, where each L-amino acid is replaced with a D-amino acid and the sequence is reversed. It also includes variants of αMSH where one or more of the amino acids of αMSH is replaced with the corresponding D amino acid. It also includes circularized versions of the forward L and reverse D sequence of any of these specific peptides listed in this paragraph, where the N and C terminal amino acids are linked in a peptide bond to form a circular peptide. The analogues may optionally be N-acetylated and/or C-amidated.

The term "αMSH analogue" as used herein also includes any other peptide that binds to the melanocortin receptors with at least 10% of the affinity of αMSH (i.e., has a $K_D$ for the receptors no more than ten times the $K_D$ of αMSH assayed with human dermal fibroblasts), and activates the melanocortin receptors with at least 25% of the activity of αMSH (i.e., causes at least 25% as much increase in intracellular cAMP in an in vitro stimulation assay with human dermal fibroblasts relative to unstimulated control cells as does αMSH).

The affinity binding assay can be performed as described in Bohm, et al., 2004, *Proc. Nat'l. Acad. Sci. USA* 279:6959-6966. Human dermal fibroblasts, which may be purchased from the American Type Culture Collection, are cultured in RMPM 1640, 1% glutamine, 1% penicillin/streptomycin, 10% fetal calf serum. αMSH can be radioiodinated with $^{125}$I by the chloramine T method. To assay binding, cells are cultivated on a 96-well plate, then washed with binding buffer (growth medium lacking fetal calf serum). A mixture of $^{125}$I-αMSH (0.2 nM) and varying concentrations of unlabelled αMSH or the test analogue are added to each well. After incubation for 1 hour, the cells are washed with binding buffer, then detached with 0.2M NaOH. The radioactivity of the detached cells is counted by scintillation counting. The $K_D$ is the concentration of ligand that reduces specific binding of the $^{125}$I-αMSH by 50%.

For the activity assay, human dermal fibroblasts ($2 \times 10^4$ cells/well) are seeded onto 96-well tissue culture plates in regular culture medium. On the next day, they are washed with binding buffer. Subsequently they are incubated in binding buffer for 48 hours, followed by stimulation with αMSH or the test analogue at various concentrations for 20 minutes in the presence of isobutylmethylxanthine (IBMX). IBMX is a phosphodiesterase inhibitor that stabilizes the concentration of cAMP. Cells are subsequently lysed, and cAMP is determined by a commercial immunoassay (Amersham). This procedure is described in Bohm et al., 2005, *Endocrinology* 146:4635-4646.

Five melanocortin receptors are known—MC-1R, MC-2R, MC-3R, MC-4R, and MC-5R. Human dermal fibroblasts have more than one of these receptors, so the assays described above of binding to and activating the receptors on human dermal fibroblasts represent composite binding to more than one type of melanocortin receptor. But MC-1R is thought to be the primary melanocortin receptor in human dermal fibroblasts.

In particular embodiments, the MSH analogue is a peptide that binds to the melanocortin receptors with at least 10% of the affinity of αMSH, and activates the melanocortin receptors with at least 25% of the activity of αMSH.

In particular embodiments the MSH analogue is a peptide that binds to the melanocortin receptors with at least 25% or at least 50% of the affinity of αMSH.

In particular embodiments, the MSH analogue is a peptide that activates the melanocortin receptors with at least 50% or at least 100% of the activity of αMSH.

In particular embodiments, the MSH analogue binds to the melanocortin receptors with at least 50% of the affinity of αMSH or activates MC-1R at least 50% as much as αMSH does.

In specific embodiments, the composition comprises an αMSH analogue that is at least 84%, at least 75%, or at least 69% identical to SEQ ID NO:1.

In specific embodiments, the composition comprises αMSH.

In specific embodiments, the composition comprises 0.05% to 2.0%, 0.1% to 1%, 0.1% to 0.5%, or 0.2% to 0.4% αMSH by (w/v).

In specific embodiments, the composition comprises a penetration enhancer. Penetration enhancers that may be included in the compositions include TRANSCUTOL (2-(2- ethoxyethoxy)ethanol), 1-methylpyrolidone (NMP), LABRASOL (caprylcaproyl macrogol glycerides), D-alpha tocopheryl polyethylene glycol 1000 succinate (TPGS), and dimethylsulfoxide (DMSO). TPGS is a vitamin E derivative esterified to polyethylene glycol 1000.

In specific embodiments, the composition comprises TRANSCUTOL. The TRANSCUTOL concentration in some compositions is at least 10%, at least 20%, or at least 30% (w/v).

In specific embodiments, the composition comprises NMP. The NMP concentration in the compositions in specific embodiments is at least 1%, at least 2%, at least 3%, or at least 5% (w/v).

In specific embodiments, the composition comprises both TRANSCUTOL and NMP. As shown in the Example below, the combination of TRANSCUTOL and NMP synergistically enhanced skin absorption of αMSH substantially more than either alone.

In specific embodiments, the composition comprises at least 30% TRANSCUTOL and at least 5% NMP.

In specific embodiments, application of the composition to rat skin gives retention of at least 0.75 mg αMSH per mg of epidermis in a Franz diffusion cell permeation assay, as described in the Example below.

In specific embodiments, the composition is more effective than PROTOPIC in reducing ear thickness 96 hours after challenge with hapten in an allergic contact dermatitis assay with mouse ears, as described in the Example below.

In particular embodiments, the composition is more effective than PROTOPIC in reducing inflammatory infiltrate into mouse ear tissue 96 hours after challenge with hapten in an allergic contact dermatitis assay with mouse ears, as described in the Example below.

The topical pharmacological compositions of the invention are adapted for delivery through the skin. They typically include a pharmaceutically acceptable diluents or carrier, in addition to the active agent. Useful liquid carriers for topical dermatological compositions of the invention include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

And as discussed herein, the compositions preferably include one or more penetration enhancers.

EXAMPLE

Introduction

Allergic contact dermatitis (ACD) is a delayed contact hypersensitivity reaction that develops about 24 hours following skin contact by an allergen to which the individual has been previously sensitized. Murine models of ACD are well established as a reliable way to investigate in vivo cutaneous inflammatory responses.

This study addresses the efficacy of topical application of full-length α-MSH formulated with specific vehicles and skin penetration enhancers in a murine model of established allergic contact dermatitis (ACD). We use this model to compare different treatment efficacies by ear thickness measurement 24, 48, 72, and 96 hours following elicitation of ACD. Combinations of various vehicles and penetration enhancers are utilized to increase the permeation of full-length α-MSH into the skin. In this report, we present a unique topical formulation of full-length α-MSH that effectively treats established ACD with an in vivo efficacy comparable to that of commercially available tacrolimus (PROTOPIC).

Methods

Animals and Care

Male Hairless rats (CD® hrBi) were obtained from Charles River Laboratories (Wilmington, Mass.), and skin prepared from euthanized animals was used for in vitro permeation and retention experiments. Female mice (C57BL/6) were purchased from Harlan Sprague Dawley (Chicago, Ill., USA) and were used for the allergic contact dermatitis (ACD) model in vivo. All animals were housed at the institutional animal facility in microisolator containers with free access to water and food. Care for animals was in accordance with institutional guidelines, and experiments were carried out as written in the approved protocols. Mice were briefly anesthetized for treatment and measurement using isoflurane.

Reagents

α-MSH (assay >95%) was custom synthesized and stored at −22° C. as supplied (Biopeptide Co., Inc., San Diego, Calif.). Ethanol USP (200 proof) was obtained from Florida Distillers Co. (Lake Alfred, Fla.). N-methyl-2-pyrrolidone (NMP) and 2,4-dinitro-1-flurobenzene (DNFB) were procured from Sigma Chemical Co. (St. Louis, Mo.). The dermatological vehicles LABRASOL (LS), Transcutol® (TC), and propylene glycol (PG) were provided by GATTEFOSSE, Inc. (Saint-Priest Cedex, France). D-alpha tocopheryl polyethylene glycol 1000 succinate (TPGS) was provided by Eastman Company UK Ltd. (Anglesey, UK). Betamethasone dipropionate ointment USP (0.05% w/w) (Actavis, Lincolnton, N.C.). PROTOPIC ointment (0.1% tacrolimus w/w) (Astellas Pharma US, Inc., Deerfield, Ill.), and AQUAPHOR ointment from EUCERIN (Beiersdorf Inc., Wilton, Conn.) were obtained from a commercial pharmacy. Dexamethasone was formulated as a 0.5 mM (0.02% w/v) solution in the same vehicle combination as the corresponding α-MSH formulation within each experiment.

In Vitro Skin Permeation and Retention Experiments

In order to determine if the penetration and retention of full-length α-MSH could be augmented in vitro by formulations containing compounds known to improve this process, we conducted in vitro studies with 36 different formulations of α-MSH. The α-MSH powder was weighed directly into a 2 mL graduated glass vial and dissolved in water. Measured volumes of the respective vehicles were dissolved in the solution to achieve the desired percentage (w/v) of α-MSH. Hairless rats were euthanized, skin from the dorsal surface was excised, and the adherent fat and subcutaneous tissue were removed. The skin was mounted on Franz diffusion cells with the stratum corneum facing the donor compartment. The volume of the donor and receptor cells was 2.0 and 5.0 mL, respectively.

Permeation of α-MSH in these formulations was measured by applying the formulation (200 μL) on the skin surface in the donor compartment, sealed with aluminum foil and Parafilm®. The receptor compartment was filled with pH 7.4 phosphate-buffered saline (PBS) containing 10% ethanol, which was stirred at 300 rpm and maintained at 37° C. using a circulating water bath. Ethanol was added to the PBS to increase the solubility of α-MSH. After 24 hours, the receptor compartment was sampled, and α-MSH content was analyzed by HPLC.

For the retention studies, the donor cell was removed, and the excess formulation was removed from the surface of the skin by gently wiping with a cotton swab dipped in 50% ethanol. The skin was then washed with 2×0.5 mL 50% ethanol in water and blotted dry with lint-free absorbent wipes.

The application area (0.636 cm$^2$) was collected with a biopsy punch. α-MSH retained in the epidermis and the dermis was extracted using a previously reported method (21). The samples were homogenized and boiled for 10 minutes in acetic acid (1M) followed by centrifugation. The α-MSH content of each sample was analyzed by HPLC. These experiments were repeated at least 3 times using skin samples from different rats.

High-Performance Liquid Chromatography Assay

Analysis of α-MSH in permeation and retention studies conducted in vitro with skin from hairless rats was performed using an HPLC system (Waters Corp, Milford, Mass.) operated by Millennium software. The HPLC system consisted of an autosampler (model 717 plus), two pumps (model 515), a photodiode array UV detector (model 996) and a reverse phase $C_{18}$ analytical column (5 μm, 4.6×250 mm, 300 Å pore size silica) (GraceVydac, Columbia, Md.). The mobile phases used were 0.1% TFA in water (solvent A) and 0.1% TFA in acetonitrile (solvent B), and they were run at a gradient of 68%:32% to 32%:68% (solvent. A:B, respectively) for 30 minutes, with a flow rate of 1 mL/min. The α-MSH content in the samples was determined using the UV detector set at 230 nm, and the detection limit was determined to be 0.1 μg/mL. All HPLC injections were performed at room temperature.

Induction and Treatment of Allergic Contact Dermatitis

Allergic contact dermatitis was induced as previously described (8, 16). Mice were sensitized on day 0 by applying 25 μL of 0.5% DNFB in 4:1 acetone/olive oil on the shaved abdomen. Mice were challenged on day 5 with a single topical application of 15 μL of 0.2% DNFB in 4:1 acetone/olive oil on the right ear in order to induce an ACD response. The left ears were treated with a single topical application of the matched vehicle alone (4:1 acetone/olive oil) to serve as an internal control for the experiments. Beginning on day 6 (24 hours after challenge), the right ears were treated with 15 μL of topically applied α-MSH formulations or 0.5 mM dexamethasone solution and the left ears of the same mice were topically applied with the corresponding matched vehicle. All formulations were prepared 24 hours prior to initial treatment and were stored at 4° C. for the duration of the treatment regimen. Commercial ointment products were topically applied 20 μL per treatment as measured with a syringe and spread evenly with an applicator stick. AQUAPHOR ointment served as the matched vehicle for commercial ointment treatments. Ears were treated 24, 30, 48, 54, 72, and 78 hours following DNFB challenge to mimic a clinically-relevant treatment regimen of twice daily, once in the morning and once in the evening. The ACD response was determined by the degree of ear swelling of the hapten-exposed ear (right) compared to that of the matched vehicle-treated contra-lateral ear (left) before DNFB challenge and at 24, 48, 72, and 96 hours after challenge, as measured with a micrometer (7309, Mitutoyo, Tokyo, Japan). Percent change was determined based on 100% thickness 24 hours after challenge. Each treatment group consisted of 5 mice, and each formulation was tested in 3 to 5 independent experiments.

Immunohistochemistry

Mice examined in the allergic contact dermatitis model were euthanized 96 hours after challenge with DNFB, and the left and right ears were excised. Ears were fixed in alcoholic formalin and embedded in paraffin. Cross-sections were cut through the center of each ear anterior to posterior. Ears were stained using hematoxylin and eosin (H&E). Additionally, the inflammatory markers CD3 and ICAM-1 were stained using rat anti-mouse primary antibodies (0.2 μg/mL and 1.0 μg/mL, respectively) and detected with a mouse-absorbed goat anti-rat'horseradish peroxidase-conjugated secondary antibody (1.0 μg/mL). Endogenous peroxidase activity was blocked with $H_2O_2$ before antibody incubations and DAB exposure, and then the marker-stained slides were counterstained with Mayer's hematoxylin blued with dilute ammonium hydroxide. The sections of each ear were photographed at representative sites using a light microscope (Zeiss Axio Imager; Zeiss, Thornwood, N.Y.) with an attached digital camera (Axiocam MRc, Zeiss, Thornwood, N.Y.) operated by Zeiss AxioVision 4.6.

Results

Formulation Selection for Optimal Topical Treatment with α-MSH

In order to enhance delivery into and retention within the skin, full-length α-MSH was formulated with vehicles known to enhance skin penetration. Since α-MSH is water soluble, all of our formulations were aqueous or ethanol-based. Of the vehicles we tested in vitro, ethanol, propylene glycol, TRANSCUTOL, and LABRASOL enhanced the penetration of α-MSH the most, all with about 6.5-7.0 μg of α-MSH penetrated through 1.0 cm$^2$ of skin. All four of these vehicles exhibited at least moderate retention of α-MSH in the epidermis after 24 hours, with 1.8 mg of α-MSH retained per gram of skin when in aqueous ethanol and 0.4-0.5 mg of α-MSH retained per gram of skin when in aqueous TRANSCUTOL, LABRASOL, or propylene glycol. TRANSCUTOL (2-(2-ethoxyethoxy)ethanol) is a solvent known to enhance percutaneous penetration of compounds through the stratum corneum, and LABRASOL (caprylcaproyl macrogol glycerides) is a self-emulsifying excipient that has been shown to enhance mucosal and intestinal absorption of poorly absorbable molecules (17-20). In separate studies, the penetration enhancers N-methyl-2-pyrrolidone (NMP) and D-alpha tocopheryl polyethylene glycol 1000 succinate (TPGS) were tested for increased permeation of α-MSH through the skin barrier (data not shown). NMP is a pyrrolidone derivative known to enhance transdermal delivery, and TPGS (a vitamin E derivative esterified to polyethylene glycol 1000) is a surfactant thought to enhance transdermal delivery by means of interaction with lipids of the stratum corneum (21-24). Of 36 α-MSH formulations created and examined, the 8 most effective carrier vehicle combinations with 0.25% α-MSH are listed in Table 1.

TABLE 1

α-MSH (0.25%) formulations with constituent vehicles and enhancers

| | Vehicles | | | | Enhancers | | |
|---|---|---|---|---|---|---|---|
| Formulation | PG | TC | LS | EtOH | NMP | TPGS | Water |
| MF19 | 50% | | | 40% | 10% | | |
| MF21 | | 50% | | | 10% | | 40% |
| MF25 | | 50% | | 50% | | | |
| MF27 | | | 50% | 50% | | | |
| MF30 | | | 50% | 40% | 10% | | |
| MF32 | | 50% | | 40% | 10% | | |
| MF35 | | | | 40% | | 5% | 60% |
| MF36 | | 50% | | | | 5% | 50% |

*PG: propylene glycol,
TC: transcutol,
LS: labrasol,
NMP: 1-methyl-2-pyrrolidone,
TPGS: D-alpha tocopheryl polyethylene glycol 1000 succinate, and
EtOH: ethanol.

Figure 1:
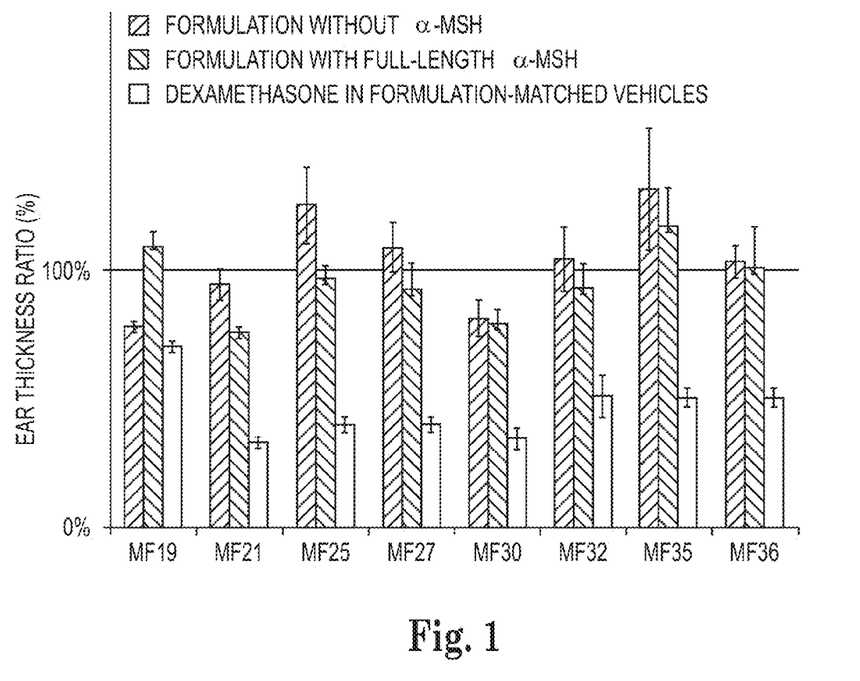

Using the murine allergic contact dermatitis (ACD) hypersensitivity model, α-MSH was tested in vivo with various combinations of these vehicles and penetration enhancers to determine the most clinically effective formulation. Based on the greatest decrease in swelling of the ACD-affected ear 24 hours after the first treatment as compared to the effect of the corresponding matched vehicle combination without α-MSH, formulation MF21 exhibited the best anti-inflammatory treatment results in vivo (FIG. 1). This formulation is composed of 0.25% α-MSH with 50% TRANSCUTOL and 10% NMP in water. α-MSH dose response studies were conducted with concentrations of 0.125%, 0.25%, and 0.5% in many topical formulations including MF21 (data not shown). The concentration of 0.25% α-MSH consistently exhibited an optimal reduction in ear swelling and was thus selected for further studies.

Permeation and Retention of Full-Length α-MSH in Hairless Rat Skin In Vitro

Figure 2:
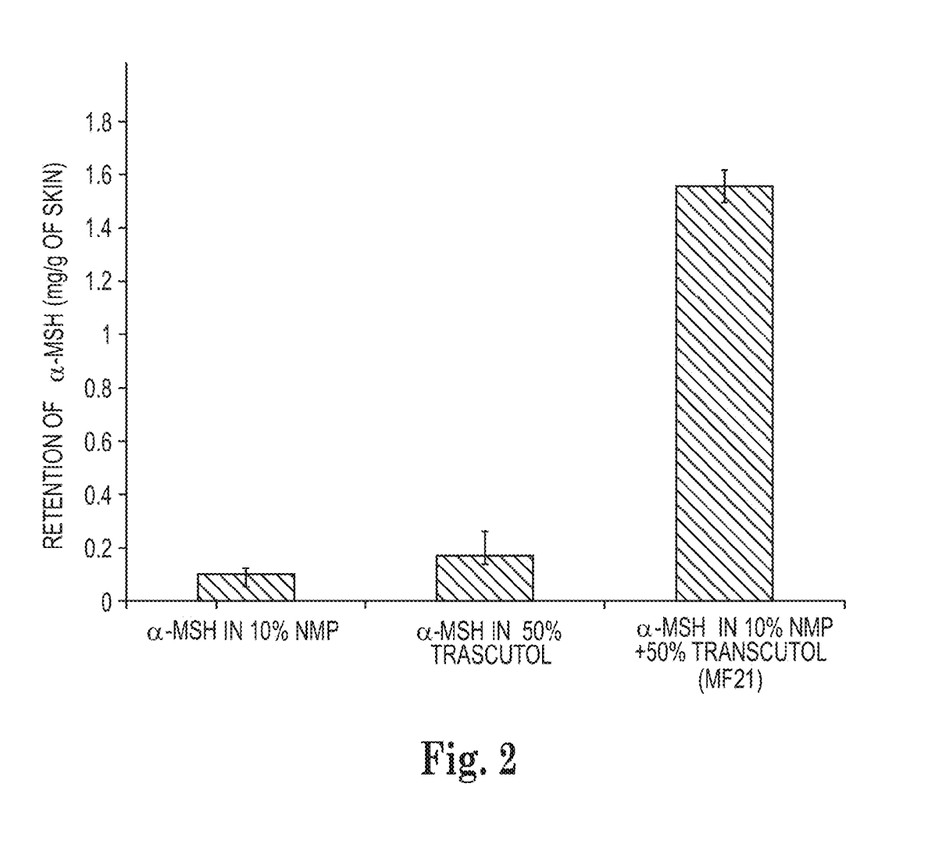
FIG. 2. α-MSH penetration into and retention within rat skin is dependent upon the combination of vehicles and enhancers in which it is dissolved. Franz diffusion cells were used to determine the permeation of α-MSH into hairless rat skin and the degree to which it was retained in the skin in vitro. Retention in the skin of α-MSH in formulation MF21 (0.25% α-MSH, 50% Transcutol®, and 10% NMP in water) after 24 hours was compared to the retention of α-MSH formulated only with the vehicle component Transcutol® (50% in water) or with the enhancer NMP (10% in water). All values are presented as mean±standard error of the mean (SEM).

The most promising α-MSH formulation for treatment of murine ACD in vivo (MF21: 0.25% α-MSH, 50% TRANSCUTOL, and 10% NMP in water) was tested on rat skin in vitro to measure the penetration and retention of α-MSH in the skin (FIG. 2). In the absence of TRANSCUTOL and NMP, aqueous α-MSH did not permeate through the skin barrier at all after 24 hours. Addition of only NMP (10% v/v) or only TRANSCUTOL (50% v/v) increased the penetration of α-MSH into the skin only slightly (0.10±0.02 and 0.17±0.09 mg of α-MSH retained per mg of epidermis, respectively). Addition of 10% NMP and 50% TRANSCUTOL together (formulation MF21) significantly enhanced the permeation of α-MSH into the skin after 24 hours (1.56±0.06 mg of α-MSH retained per mg of epidermis). These results strongly indicate that this α-MSH formulation is suitable for topical delivery to treat local inflammation in the skin.

Figure 3:
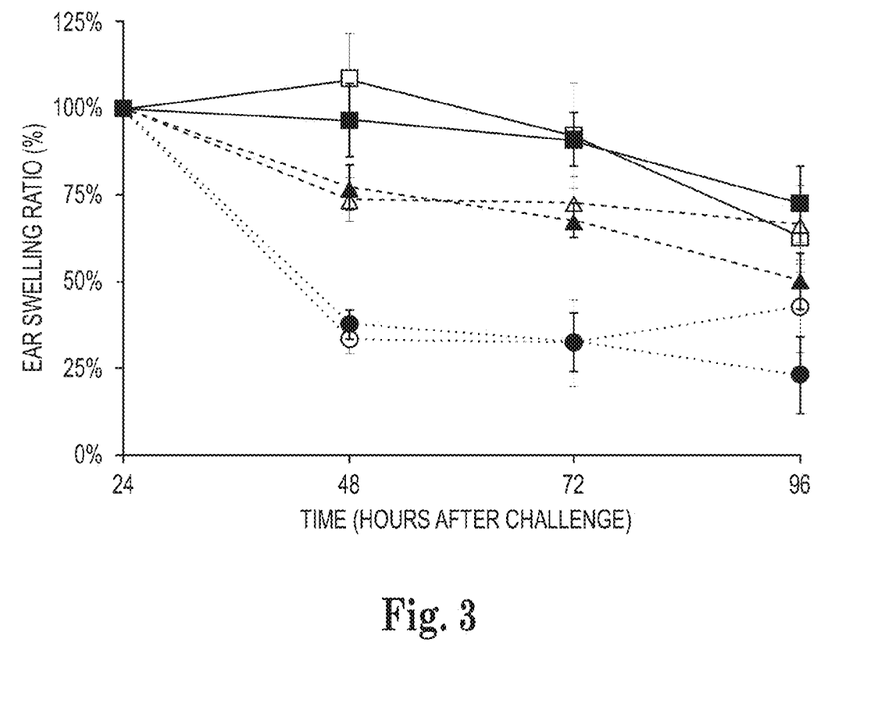

Efficacy of Full-Length α-MSH Formulation MF21 in the Treatment of Allergic Contact Dermatitis In Vivo During the treatment regimen of 24 to 96 hours following challenge with DNFB, α-MSH formulation MF21 (0.25% α-MSH, 50% TRANSCUTOL, and 10% NMP in water) steadily decreased ear inflammation in vivo with similar or slightly better effectiveness than commercially available tacrolimus ointment (PROTOPIC) (FIG. 3). The corticosteroids dexamethasone (0.5 mM in the same vehicle-enhancer solution as MF21) and commercially available betamethasone ointment (0.05% w/w) served as positive controls and had a rapid and sustained inhibition of ear inflammation as expected. A group of mice with untreated ACD and a group of mice treated with only 50% TRANSCUTOL and 10% NMP in water (formulation-matched vehicles only) served as negative controls and had a similar inflammatory response expected for untreated ACD. This demonstrates that the vehicle components of MF21 (50% TRANSCUTOL and 10% NMP in water) were biologically non-reactive, neither increasing nor decreasing the ear swelling response. All values are expressed as mean±standard error of the mean (SEM).

Figure 4:
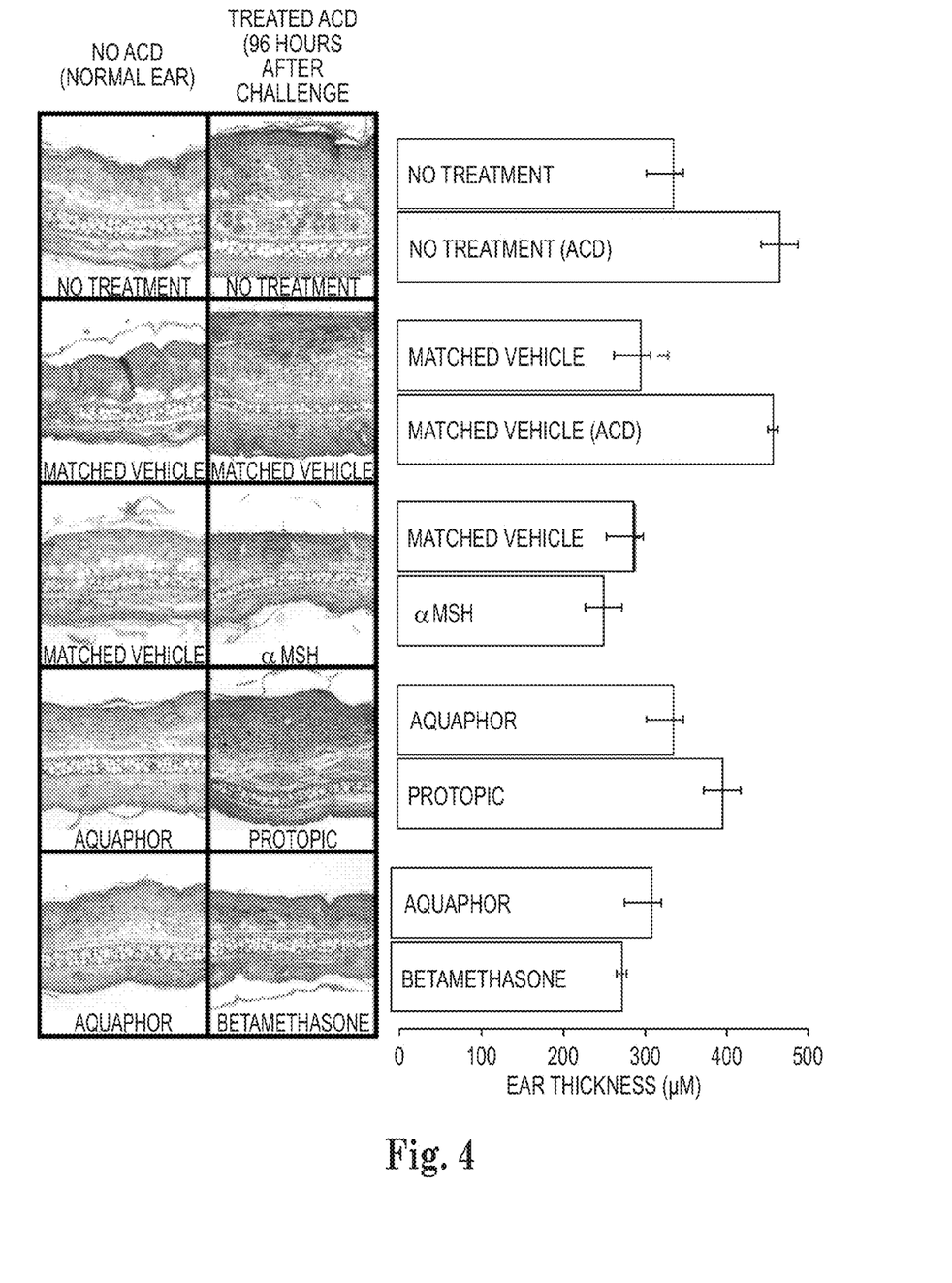
FIG. 4. Histological staining confirmed that a topical formulation of full-length α-MSH reduced ACD-induced inflammation as well as currently available topical agents. Ear tissue was excised 96 hours after challenge with DNFB, fixed in formalin, and embedded in paraffin. Thin sections (4

Immunohistochemical Analysis of α-MSH Treatment in the Hypersensitivity Model of ACD Mice used in the allergic contact dermatitis model were euthanized 96 hours after challenge with DNFB (72 hours after initiation of topical treatment), and the left and right ears were excised, fixed with formalin, and embedded in paraffin. Cross-sections of the middle of each ear (same position) were cut at a thickness of 4 μm and stained with hematoxylin and eosin (H&E). Right ears (hapten-challenged) exhibited swelling that was alleviated to different degrees with different treatment compounds applied, while the left ears (unchallenged and applied only with matching vehicles) retained a fairly constant baseline thickness and histology among the various groups (FIG. 4). The untreated group and formulation-matched vehicle-treated group demonstrated a high degree of swelling and influx of inflammatory infiltrate (two negative controls: full ACD reaction). The group treated with commercially available tacrolimus ointment (PROTOPIC) exhibited a moderate decrease in swelling but retained a higher quantity of lymphoid infiltrate than baseline. The α-MSH-treated group and the positive control group (treated with commercially available betamethasone ointment) both demonstrated a complete alleviation of swelling down to slightly below baseline thickness, and both had a relatively low retention of inflammatory infiltrate. These results suggest that α-MSH formulation MF21 exhibited a better treatment response than PROTOPIC and that α-MSH was nearly as effective as the corticosteroid betamethasone after three days of treatment applied twice per day. Microscopic measurements of thickness were made at 5 equidistant points on each of the photographed H&E sections. All values are expressed as mean±SD. All differences were statistically significant as determined by ANOVA for pair-wise comparison ($P<0.05$).

Overall, the allergic contact dermatitis hypersensitivity response developed intense perivascular lymphoid infiltrate extending into the papillary dermis with little or no change in the epidermis at 96 hours following challenge. In all samples generally >90% of the inflammatory infiltrate consisted of lymphocytes and <10% consisted of eosinophils. We employed a scale to grade the level of relative inflammation among our treatment conditions: (1+) representing few lymphocytes and eosinophils above baseline levels that are scattered around blood vessels, (2+) representing increased perivascular infiltrate, (3+) representing intense perivascular infiltrate extending slightly into the interstitial collagen between vessels within the papillary dermis, and (4+) representing intense diffuse lymphocytic infiltrate throughout the papillary dermis. Compared to baseline, non-treated ears with full ACD exhibited diffuse lymphocytic infiltrate corresponding to a score of 3+, and the vehicle-treated ears predominantly had perivascular infiltrate with slight extension of the infiltrate into the interstitium consistent with a score of 2+ to 3+. Ears treated with commercially available tacrolimus (PROTOPIC) represented a histologically intermediate response of 2+ to 3+ with many scattered perivascular lymphocytes and eosinophils surrounding the vessels of the superficial plexus and extending slightly into the interstitial collagen. Ears treated with α-MSH were given a score of 1+ with very few scattered lymphocytes and eosinophils. The α-MSH-treated biopsy demonstrated only a slight degree of increased remaining inflammation over the non-inflamed baseline achieved by treatment with commercially available betamethasone ointment (0.05%).

To assay inflammation, ear tissue of the mice was excised 96 hours after challenge with DNFB, fixed in formalin, and embedded in paraffin. Thin sections (4 μm) were blocked with $H_2O_2$, stained with rat anti-mouse primary antibodies (1.0 μg/mL ICAM-1 ab, 0.2 μg/mL CD3 ab) and a mouse-absorbed goat anti-rat secondary antibody (1.0 μg/mL), and then counterstained. ICAM-1 and CD3 were visualized with oil immersion objectives (63× and 40×, respectively). In ears with untreated ACD, intracellular adhesion molecule-1 (ICAM-1) remained highly expressed on the endothelial cells lining vessels in the dermis and on various cells scattered throughout the interstitium, as shown by immunohistochemistry (data not shown). Expression of ICAM-1 was reduced after three days of treatment with full-length α-MSH in MF21. Expression of the CD3 marker antigen in the lymphocytic infiltrate, which was heightened in an untreated ear and greatly reduced following three days of treatment with full-length α-MSH, confirmed that the hypersensitivity reaction in our model elicited a T cell-mediated inflammatory response that was specifically modulated by α-MSH. Staining patterns of both of these markers are consistent with known mechanisms of allergic contact dermatitis, which supports the validity of the results found in this study using the contact hypersensitivity mouse model to simulate the treatment of ACD (data not shown).

Discussion

Some investigators have determined that the anti-inflammatory activity of α-MSH depends largely on the c-terminal residues 11-13 (KPV, an abbreviation for lysine-proline-valine) (9, 25). A synthetic variant of the KPV tripeptide in which valine is replaced with the more polar amino acid threonine (KPT) demonstrates similar properties as KPV itself and has also been considered for therapeutic viability (15). KPV and KPT have been shown to exert anti-inflammatory activity by antagonistically binding the IL-1 receptor type I (IL1RI), which contributes to the suppression of IL-1-mediated inflammation (15). However IL-1 modulation is only one of the known effects of α-MSH, many of which are through distinct mechanisms. Much of the biological activity of α-MSH is through the binding of its main receptor, MC-1R (9). Prabhu et al. hypothesized that amino acids 7 and 9 of full-length α-MSH interact with the transmembrane portion of MC-1R and that amino acids 6 and 8 may interact with the extracellular loops of MC-1R to facilitate binding to the receptor (26). In 2003, Luger et al. found that KPV was able to bind to MC-1R and modulate the function of antigen presenting cells, but the same group discovered in 2007 that KPV may not actually bind MC-1R nor elevate cAMP levels as a result (9, 15). It is now believed that many of the anti-inflammatory activities of KPV and related peptides are through pathways not involving MC-R binding (1). Since only a portion of the known α-MSH-modulated pathways are mimicked by short c-terminal peptide derivatives, it is important to continue to study full-length α-MSH and to refine its potential treatment efficacy.

In this study, we demonstrate for the first time that topical application of full-length α-MSH formulated with a particular vehicle and enhancer in water is effective in treating skin inflammation when α-MSH is first applied only after inflammatory presentation. We utilize a mouse model that is widely accepted to closely mimic the inflammatory response of allergic contact dermatitis in humans to demonstrate the anti-inflammatory effects of topical α-MSH treatment in a clinically-relevant timeline.

Allergic contact dermatitis (ACD) is one of the most common cutaneous inflammatory disorders and can be caused by hundreds of different substances that a host recognizes as an allergen (27). These are encountered both in occupational or private settings. ACD results in spongiosis in the epidermis, dilation of the papillary vessels, perivascular lymphocytic infiltrate, and edema in the upper dermis (28). These histological observations were made in the ACD-induced tissue analyzed in this study, and these responses were noticeably alleviated following treatment with corticosteroids and α-MSH. ACD shares the histologic pattern of spongiotic dermatitis with other forms of contact dermatitis and atopic dermatitis and exhibits similar therapeutic responses to anti-inflammatory agents. The most common therapy currently used is topical application of corticosteroids. The anti-inflammatory and immunosuppressive effects of corticosteroids include changing migration patterns of leukocytes as well as inhibiting lymphokine synthesis and monocyte function (29). There are also pronounced harmful metabolic and toxic side effects, which may include skin atrophy, striae, perioral dermatitis, acne rosacea, and the potential for systemic absorption that could lead to adrenal atrophy, Cushing's syndrome, growth inhibition, hypertension, vascultits, and a host of other damaging effects on various systems (11, 29). Adverse side effects are more likely to arise from long-term application of corticosteroids.

In the last decade calcinurin inhibitors have become clinically available for the treatment of different forms of dermatitis, with tacrolimus and pimecrolimus gaining US FDA approval for the treatment of atopic dermatitis in 2000 and 2001, respectively. Tacrolimus and pimecrolimus are the most widely used calcinurin inhibitors, and each exhibits fewer adverse side effects than most corticosteroids (30, 31). However, burning, pruritis, and allergy in certain circumstances may limit their use (30-32). In 2005, the FDA issued a black box warning about the potential carcinogenic properties of tacrolimus and pimecrolimus (33). This warning significantly warrants further investigation into the safety of these drugs. In this study topical treatment with a specific α-MSH formulation had a similar clinical efficacy in the treatment of ACD with a better histological outcome as compared to commercially available tacrolimus ointment (PROTOPIC) in a mouse contact hypersensitivity model. Significant reduction of ACD-induced perivascular lymphocytic infiltrate and dermal edema achieved by betamethasone and α-MSH was only moderately achieved by PROTOPIC. In 2003 Nishimuta and Ito topically applied PROTOPIC ointment as a clinically-relevant control in a similar mouse contact hypersensitivity model and demonstrated that it moderately suppressed immediate and late phase ear edema reactions in ovalbumin-sensitized mice (34). In 2005 Bhol and Schechter also topically applied PROTOPIC ointment as a control along with the potent steroid halobetasol in a DNFB-induced contact hypersensitivity mouse model demonstrating an intermediate anti-inflammatory effect of PROTOPIC compared to that of the steroid, substantiating the findings of our current study (35). Since PROTOPIC is a widely used commercial topical therapy for dermatitis, our findings suggest that α-MSH could have similar or better clinical effectiveness and would be a valuable alternative therapeutic choice in some clinical settings.

This study provides evidence that α-MSH can be formulated with vehicles and skin-penetration enhancers commonly used in commercial preparations of topical medications to be utilized as an effective topical therapy for inflammatory skin reactions such as allergic contact dermatitis. We demonstrate that a highly effective formulation (0.25% α-MSH with 50% TRANSCUTOL and 10% NMP in water) performs at least as well as PROTOPIC in a widely accepted murine contact hypersensitivity model when applied topically after inflammation has already begun. We suggest that α-MSH is also a suitable peptide for penetrating the skin barrier in humans to deliver local anti-inflammatory effects when prepared with an ideal combination of excipients. This study is the first to employ topical treatment of full-length α-MSH in a clinically-relevant timeline to demonstrate effectiveness in the treatment of skin inflammation with the initiation of application following symptomatic presentation.

REFERENCES

1. Brzoska T, Luger T A, Maaser C, Abels C, Bohm M. Alpha-melanocyte-stimulating hormone and related tripeptides: biochemistry, antiinflammatory and protective effects in vitro and in vivo, and future perspectives for the treatment of immune-mediated inflammatory diseases. Endocr Rev 2008: 29: 581-602.
2. Mazurkiewicz J E, Corliss D, Slominski A. Spatiotemporal expression, distribution, and processing of POMC and POMC-derived peptides in murine skin. J Histochem Cytochem 2000: 48: 905-914.
3. Bohm M, Luger T A, Tobin D J, Garcia-Borron J C. Melanocortin receptor ligands: new horizons for skin biology and clinical dermatology. J Invest Dermatol 2006: 126: 1966-1975.
4. Steinhoff M, Stander S, Seeliger S, Ansel J C, Schmelz M, Luger T. Modern aspects of cutaneous neurogenic inflammation. Arch Dermatol 2003: 139: 1479-1488.
5. Bohm M, Schiller M, Luger T A. Non-pigmentary actions of alpha-melanocyte-stimulating hormone—lessons from the cutaneous melanocortin system. Cell Mol Biol (Noisy-le-grand) 2006: 52: 61-68.

6. Bhardwaj R S, Schwarz A, Becher E, et al. Pro-opiomelanocortin-derived peptides induce IL-10 production in human monocytes. J Immunol 1996: 156: 2517-2521.
7. Redondo P, Garcia-Foncillas J, Okroujnov I, Bandres E. Alpha-MSH regulates interleukin-10 expression by human keratinocytes. Arch Dermatol Res 1998: 290: 425-428.
8. Grabbe S, Bhardwaj R S, Mahnke K, Simon M M, Schwarz T, Luger T A. alpha-Melanocyte-stimulating hormone induces hapten-specific tolerance in mice. J Immunol 1996: 156: 473-478.
9. Luger T A, Scholzen T E, Brzoska T, Bohm M. New insights into the functions of alpha-MSH and related peptides in the immune system. Ann N Y Acad Sci 2003: 994: 133-140.
10. Luger T A, Scholzen T, Grabbe S. The role of alpha-melanocyte-stimulating hormone in cutaneous biology. J Investig Dermatol Symp Proc 1997: 2: 87-93.
11. Berger T G, Duvic M, Van Voorhees A S, VanBeek M J, Frieden I J. The use of topical calcineurin inhibitors in dermatology: safety concerns. Report of the American Academy of Dermatology Association Task Force. J Am Acad Dermatol 2006: 54: 818-823.
12. Saitta P, Brancaccio R. Allergic contact dermatitis to pimecrolimus. Contact Dermatitis 2007: 56: 43-44.
13. Shaw D W, Maibach H I, Eichenfield L F. Allergic contact dermatitis from pimecrolimus in a patient with tacrolimus allergy. J Am Acad Dermatol 2007: 56: 342-345.
14. Shaw D W, Eichenfield L F, Shainhouse T, Maibach H I. Allergic contact dermatitis from tacrolimus. J Am Acad Dermatol 2004: 50: 962-965.
15. Luger T A, Brzoska T. alpha-MSH related peptides: a new class of anti-inflammatory and immunomodulating drugs. Ann Rheum Dis 2007: 66 Suppl 3: iii52-55.
16. Scholzen T E, Steinhoff M, Sindrilaru A, et al. Cutaneous allergic contact dermatitis responses are diminished in mice deficient in neurokinin 1 receptors and augmented by neurokinin 2 receptor blockage. Faseb J 2004: 18: 1007-1009.
17. Harrison J E, Watkinson A C, Green D M, Hadgraft J, Brain K. The relative effect of Azone and Transcutol on permeant diffusivity and solubility in human stratum corneum. Pharm Res 1996: 13: 542-546.
18. Fernandez S, Jannin V, Rodier J D, Ritter N, Mahler B, Carriere F. Comparative study on digestive lipase activities on the self emulsifying excipient Labrasol, medium chain glycerides and PEG esters. Biochim Biophys Acta 2007: 1771: 633-640.
19. Hu Z, Tawa R, Konishi T, Shibata N, Takada K. A novel emulsifier, labrasol, enhances gastrointestinal absorption of gentamicin. Life Sci 2001: 69: 2899-2910.
20. Mura P, Faucci M T, Bramanti G, Corti P. Evaluation of transcutol as a clonazepam transdermal permeation enhancer from hydrophilic gel formulations. Eur J Pharm Sci 2000: 9: 365-372.
21. Payan J P, Boudry I, Beydon D, et al. Toxicokinetics and metabolism of N-[(14)C]N-methyl-2-pyrrolidone in male Sprague-Dawley rats: in vivo and in vitro percutaneous absorption. Drug Metab Dispos 2003: 31: 659-669.
22. Babu R J, Pandit J K. Effect of penetration enhancers on the release and skin permeation of bupranolol from reservoir-type transdermal delivery systems. Int J Pharm 2005: 288: 325-334.
23. Sheu M T, Chen S Y, Chen L C, Ho H O. Influence of micelle solubilization by tocopheryl polyethylene glycol succinate (TPGS) on solubility enhancement and percutaneous penetration of estradiol. J Control Release 2003: 88: 355-368.
24. Mu L, Seow P H. Application of TPGS in polymeric nanoparticulate drug delivery system. Colloids Surf B Biointerfaces 2006: 47: 90-97.
25. Kannengiesser K, Maaser C, Heidemann J, et al. Melanocortin-derived tripeptide KPV has anti-inflammatory potential in murine models of inflammatory bowel disease. Inflamm Bowel Dis 2008: 14: 324-331.
26. Prabhu N V, Perkyns J S, Pettitt B M. Modeling of alpha-MSH conformations with implicit solvent. J Pept Res 1999: 54: 394-407.
27. Kimber I, Basketter D A, Gerberick G F, Dearman R J. Allergic contact dermatitis. Int Immunopharmacol 2002: 2: 201-211.
28. Saint-Mezard P, Rosieres A, Krasteva M, et al. Allergic contact dermatitis. Eur J Dermatol 2004: 14: 284-295.
29. Schacke H, Docke W D, Asadullah K. Mechanisms involved in the side effects of glucocorticoids. Pharmacol Ther 2002: 96: 23-43.
30. Cohen D E, Heidary N. Treatment of irritant and allergic contact dermatitis. Dermatol Ther 2004: 17: 334-340.
31. Grassberger M, Steinhoff M, Schneider D, Luger T A. Pimecrolimus—an anti-inflammatory drug targeting the skin. Exp Dermatol 2004: 13: 721-730.
32. Belsito D, Wilson D C, Warshaw E, et al. A prospective randomized clinical trial of 0.1% tacrolimus ointment in a model of chronic allergic contact dermatitis. J Am Acad Dermatol 2006: 55: 40-46.
33. Ring J, Mohrenschlager M, Henkel V. The US FDA 'black box' warning for topical calcineurin inhibitors: an ongoing controversy. Drug Saf 2008: 31: 185-198.
34. Nishimuta K, Ito Y. Effects of metronidazole and tinidazole ointments on models for inflammatory dermatitis in mice. Arch Dermatol Res 2003: 294: 544-551.
35. Bhol K C, Schechter P J. Topical nanocrystalline silver cream suppresses inflammatory cytokines and induces apoptosis of inflammatory cells in a murine model of allergic contact dermatitis. Br J Dermatol 2005: 152: 1235-1242.

All patents, patent applications, and other references cited herein are hereby incorporated by reference.

What is claimed is:

1. A method of treating an inflammatory skin disorder in a human comprising:
   topically applying to the skin a composition comprising alpha-melanocyte stimulating hormone (αMSH) or an αMSH analogue in an amount effective to reduce skin inflammation in the human;
   wherein the composition comprises at least 30% 2-(2-ethoxyethoxy)ethanol and at least 5% NMP;
   wherein the αMSH analogue comprises KPV, dKPV, KPdV, dKPdV, KPT, or [Nle4,d-Ph7]αMSH; and
   wherein the αMSH or αMSH analogue is optionally N-acetylated on its N-terminus or C-amidated on its C terminus, or both, or circularized.

2. The method of claim 1 wherein the inflammatory skin disorder is allergic contact dermatitis.

3. The method of claim 1 wherein the inflammatory skin disorder is an eczematous inflammatory disorder.

4. The method of claim 1 wherein the inflammatory disorder is atopic dermatitis.

5. The method of claim 1 wherein the composition comprises αMSH.

6. The method of claim 1 wherein the composition comprises 0.1% to 0.5% αMSH (w/v).

7. The method of claim 1 wherein the composition comprises an MSH analogue comprising a peptide at least 84% identical to SYSMEHFRWGKPV (SEQ ID NO:1).

8. The method of claim 1 wherein the composition comprises an MSH analogue and the MSH analogue comprises KPV, dKPV, KPdV, dKPdV, KPT, or [Nle4,d-Ph7]αMSH.

9. The method of claim 1 wherein the composition comprises an MSH analogue and the MSH analogue is a compound that binds to the melanocortin receptors with at least 10% of the affinity of αMSH, and activates the melanocortin receptors with at least 25% of the activity of αMSH.

10. The method of claim 1 wherein application of the composition to rat skin gives retention of at least 0.75 mg αMSH per mg of epidermis in a Franz diffusion cell permeation assay.

11. The method of claim 1 wherein the composition is more effective than 0.1% tacrolimus ointment in reducing ear thickness 96 hours after challenge with hapten in an allergic contact dermatitis assay with mouse ears.

12. The method of claim 1 wherein the composition comprises an αMSH analogue, wherein the αMSH analogue consists of KPV, dKPV, KPdV, dKPdV, KPT, or [Nle4,d-Ph7]αMSH.

* * * * *